United States Patent
Hamburger et al.

[11] Patent Number: 5,969,622
[45] Date of Patent: Oct. 19, 1999

[54] ALLERGEN DETECTOR SYSTEM AND METHOD

[75] Inventors: Robert N. Hamburger, 9485 La Jolla Shore Dr., LaJolla, Calif. 92037; Ruibo Wang; Jien-Ping Jiang, both of Tucson, Ariz.; Donald Kaminski, deceased, late of Hattiesburg, Miss., by Alice Mae Smith Kaminski, Administraix; Mark Castracane, Hattiesburg, Miss.

[73] Assignee: Robert N. Hamburger, La Jolla, Calif.

[21] Appl. No.: 09/005,408

[22] Filed: Jan. 9, 1998

Related U.S. Application Data

[63] Continuation-in-part of application No. 08/946,288, Oct. 7, 1997.

[51] Int. Cl.$^6$ .................................................. G08B 21/00
[52] U.S. Cl. ....................... 340/627; 340/630; 250/564; 250/574; 356/438; 116/214
[58] Field of Search ................................ 340/627, 630; 250/564, 565, 573, 574; 356/337, 33 P, 439, 438; 73/28.01, 28.04, 863.21–863.24; 116/214

[56] References Cited

U.S. PATENT DOCUMENTS

| | | |
|---|---|---|
| 3,845,480 | 10/1974 | Steinberg . |
| 3,867,640 | 2/1975 | Paulsen . |
| 4,175,865 | 11/1979 | Horvath et al. . |
| 4,226,533 | 10/1980 | Snowman . |
| 4,583,859 | 4/1986 | Hall, II . |
| 4,830,494 | 5/1989 | Ishikawa et al. . |
| 4,839,529 | 6/1989 | Freungel . |
| 5,001,463 | 3/1991 | Hamburger ............................. 340/627 |
| 5,305,072 | 4/1994 | Sawada et al. . |
| 5,315,115 | 5/1994 | Gerber . |
| 5,383,024 | 1/1995 | Maxey et al. . |
| 5,416,580 | 5/1995 | Trainer . |
| 5,426,501 | 6/1995 | Hokanson et al. . |
| 5,428,964 | 7/1995 | Lobodell . |
| 5,646,597 | 7/1997 | Hamburger et al. .................... 340/627 |

FOREIGN PATENT DOCUMENTS

| | | |
|---|---|---|
| 01247153 | 5/1991 | Japan . |
| 8233723 | 9/1996 | Japan . |
| 1298658 | 12/1972 | United Kingdom . |
| 2044445 | 1/1980 | United Kingdom . |

OTHER PUBLICATIONS

Casswell et al., Simslin II—A Portable Airborne Dust Measuring Instrument Employing A Light Scattering Technique, Conference Article, Aug. 1978, 20–1 –20–12.

*Primary Examiner*—Daniel J. Wu
*Attorney, Agent, or Firm*—Brown Martin Haller & McClain LLP

[57] ABSTRACT

An allergen particle detecting apparatus has a sample area through which environmental air is directed. A light beam is directed through the air sample so that portions of the beam will be scattered if any particles are present in the path of the beam. A beam blocking device on the opposite side of the air sample is arranged to block all light except light scattered in a predetermined angular range corresponding to a predetermined allergen particle size range. Light transmitted through the blocking device is detected by a light detector and an alarm output signal is produced if the detected amount of light is above a predetermined level.

4 Claims, 1 Drawing Sheet

ALLERGEN DETECTOR SYSTEM AND METHOD

This application is a continuation-in-part of pending U.S. application Ser. No. 08/946,288 filed Oct. 07, 1997.

BACKGROUND OF THE INVENTION

The present invention is directed to a system and method for detecting airborne allergen particles and for providing an alarm or operating a filtering system if the detected amount of allergen particles is above a predetermined level.

Many individuals suffer from allergies to airborne particles such as dust, pollen and the like which are often present in the environmental air breathed by the individual. The majority of particulates to which many individuals are sensitive are typically in the 5 to 50 micron range. The presence of such particles in air breathed by sensitive or allergic individuals may give rise to a plethora off symptoms such as asthma, coughing, sneezing, as well as skin rashes and anaphylaxis. Knowledge or warning of the presence of high levels of allergenic particles in the environmental air is helpful to such individuals, potentially enabling them to take medication, leave the area, or activate allergen removing filters before the onset of serious symptoms.

In U.S. Pat. No. 5,001,463 (Hamburger) an allergen particulate detecting apparatus is described wherein air is blown through a passageway in which an allergen particle sensor is mounted for sensing allergen-sized particles. The output signal of the sensor is dependent on the amount of sensed particles, and an alarm is activated if the signal is above a predetenrnied level.

U.S. Pat. No. 5,646,597 (Hamburger, et al.) describes a system and method for detecting concentrations of particles in a given range of sizes by directing a light beam through a sample of environmental air and measuring the amount of light which is scattered by particles within the sample. A beam blocking device is provided which blocks the focused, unscattered portion of the light beam. A discriminator is also provided which allows the device to detect only those particles which are within the size range of approximately 5 to 50 microns. Pending application Ser. No. 08/771,641 provides an improvement in the discriminating apparatus of the '597 patent.

One problem with the devices described in the prior art which utilizes lasers arises when an inexpensive laser is used as the light source. In addition to the light that is focused on the beam blocking device, a certain amount of light "noise" is also produced. This noise can cause false readings if mistaken by the detector for light scattered by particles in the air sample. The present invention describes an optical configuration wherein the light noise produced by the laser is also blocked, thus preventing the device from detecting the noise as light scattered by particles in the air sample.

SUMMARY OF THE INVENTION

In the present invention, an allergen particle detection system is provided which comprises a light source for directing a light beam through a sample of environmental air, and a beam blocking and focusing assembly positioned in the light path on the opposite side of the air sample which blocks the transmission of all light, including noise generated by the light source, except the portion of light scattered in a predetermined angular range. The scattered light is focused on a detector positioned to receive light transmitted through the beam blocking assembly, and a control circuit is connected to the detector for generating an alarm output signal if the detector output is above a predetermined level.

The alarm output signal may be used to activate an audible or visual alarm device, or to turn on a filtration and ventilation system including HEPA or allergen particle filters. The filtration system may be turned off as soon as the detected allergen particles have returned to a safe level. The apparatus may be relatively small, and may be conveniently designed for wall mounting.

In the preferred embodiment, the allergen detection device is contained in a darkened tube-like housing. The laser light source is disposed at one end of the housing and transmits a light beam through a sample of environmental air which has been refreshed by a fan mounted in the side of the housing. The beam blocking and focusing assembly is disposed opposite the air sample from the laser and comprises two lenses mounted on the optical axis of the device such that the scattered light is transmitted through both lenses and focused on an optical detector. The first lens has a circle of light blocking material centered on the optical axis of the device. The light blocking material is of a predetermined diameter sized to block all unscattered light from the laser, and light scattered at angles below a predetermined minimum angle, which is scattered by particles larger than the largest allergen particle size. Scattered light which exceeds the maximum scattering angle is absorbed by the darkened walls of the detector housing, and are thereby also effectively blocked. The first lens transmits scattered light that falls within the predetermined angular range through to the second lens, which focuses it on an optical detector mounted at the end of the housing opposite the laser light source. Noise which is emitted by the laser is focused by the first lens onto a circle of light blocking material which is mounted on the second lens on the optical axis of the device. The noise is thereby prevented from being focused on the optical detector by the second lens and is effectively blocked.

In the preferred embodiment, the dimensions of the blocking and focusing assembly were arranged to block all light except that scattered by particles in the size range of 5 to 50 microns.

According to another aspect of the present invention, a method of detecting the presence and concentration of allergen particles in the air is provided which comprises the steps of directing a light beam through a sample of environmental air such that light will be scattered by any particles in the air, blocking unscattered light, light scattered outside a predetermined angle range and noise produced by the light source, transmitting only light within the predetermined range of scattering angle, focusing the transmitted light, detecting the focused, transmitted light and producing an output signal at a level proportional to the amount of light transmitted, and generating an alarm signal if the output signal is above a predetermined level.

This system and method readily discriminates between allergen size particles in the 5 to 50 micron range and larger, non-allergenic particles so as to produce an accurate indication of the allergen particle levels in a room or enclosed area. Preferably, the level at which the alarm signal is produced is adjustable. The apparatus can be readily connected to turn on auxiliary air cleaning appliances or filters such as HEPA filters.

BRIEF DESCRIPTION OF THE DRAWINGS

The present invention will be better understood from the following detailed description of a preferred embodiment of the invention, taken in conjunction with the accompanying drawings, in which like reference numerals refer to like parts, and in which.

DESCRIPTION OF THE PREFERRED EMBODIMENTS

Figure 1:
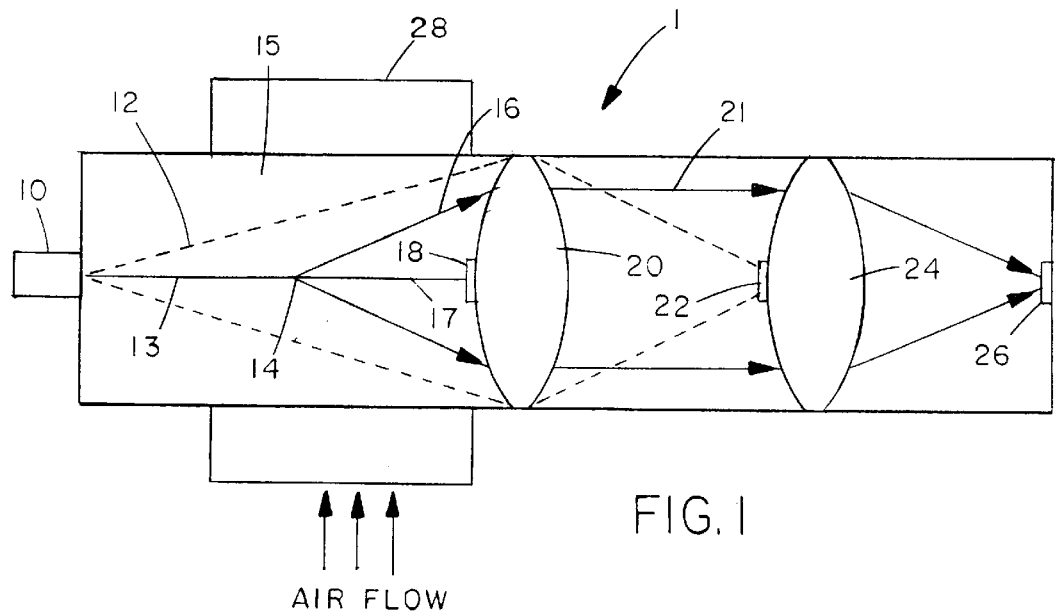
FIG. 1 is a schematic block diagram of the optical system.

FIGS. 1 and 2 of the drawings illustrate an allergen particle detector apparatus 1 according to the preferred embodiment of the present invention. Referring to FIG. 1, the apparatus comprises light source 10, which is preferably a laser. Light source 10, in the preferred embodiment is a 660 nanometer wavelength laser diode, but, as recognized by one skilled in the art, an inexpensive laser diode of any wavelength could be used with equal success. Although a laser diode in the infrared or visible light range is used as the light source in the preferred embodiment of the invention, other light sources may be used such as other types of laser emitters, for example a He-Ne laser with a wavelength of 0.6328 micron, or other light sources with collimators for producing a coherent light beam, such as light emitting diodes in the visible or infrared light range. The light is preferably infrared, but may alternatively be visible light.

Light source 10 shines focused light beam 13 through air sample 15 within detector 1. When focused light beam 13 strikes particle 14 within air sample 15, a portion of focused light beam 13 is deflected or scattered. The scattered portion 16 of focused light beam 13 thus represents the presence of a particle within air sample 15. The unscattered portion 17 of focused light beam 13 is blocked from reaching detector 26 by blocking member 18, which, in the preferred embodiment is a piece black material capable absorbing light, which is adhered to lens 20. Blocking member 18 must have an area which is greater than or equal to the cross-sectional area of the unscattered portion 17 of focused light beam 13. Blocking member 18 is preferably circular in shape, but need not be shaped as a perfect circle. The actual shape of blocking member 18 should correspond to the cross sectional shape of light beam 13, which could, for example, comprise an oval. In the preferred embodiment, blocking member 18 is circular, having a diameter of approximately 15 mm, or about 2 mm greater than the diameter of focused light beam 13. It is desirable to make the diameter of blocking member 18 larger than the diameter of focused light beam 13 to allow for variations in the diameter of focused light beam 13 due to deviations from the manufacturing specifications of light source 10 from unit to unit. Ideally, blocking member 18 is sized and positioned so as to block all of the unscattered portion 17 of focused light beam 13.

Blocking member 18 is a non-regular, darkened surface which will not reflect light, or which will reflect a very minimal amount of light. In the preferred embodiment, a flat black piece of the "loop" or fuzzy side of a "hook and loop" type fastener, such as Velcro,™ may be used as blocking member 18. Alternatively, blocking member 18 may also be composed of a piece of black felt. The preferred color for blocking member 18 is black, such that the maximum amount of light is absorbed.

Light source 10, in addition to focused light beam 13, also generates a certain amount of noise 12 from the surface thereof. Noise 12 is focused by lens 20 onto circular member 22, where it is blocked from reaching detector 26. In the preferred embodiment, lens 20 is approximately 40 mm in diameter, has a focal length of 40 mm and is located approximately 80 mm from the surface of light source 10. Circular member 22 is identical to blocking member 18, except that it is adhered to lens 24 instead of lens 20.

Scattered portion 16 of focused light beam 13 is transmitted through lens 20, shown in FIG. 1 as 21. Lens 24 focuses transmitted scattered light 21 onto detector 26. In the preferred embodiment, lens 24 is identical to lens 20 and is located approximately 137 mm from light source 10. Detector 26, in the preferred embodiment, is located approximately 173 mm from light source 10.

Detector 26 is a standard, commercially available photodetector which produces a voltage that is a function of the quantity of light which falls upon it. Light source 10, blocking member 18, lens 20, circular member 22, lens 24 and detector 26 are aligned with each other along a common axis, and can be mounted in housing 30 such as is shown in FIG. 2.

Figure 2A:
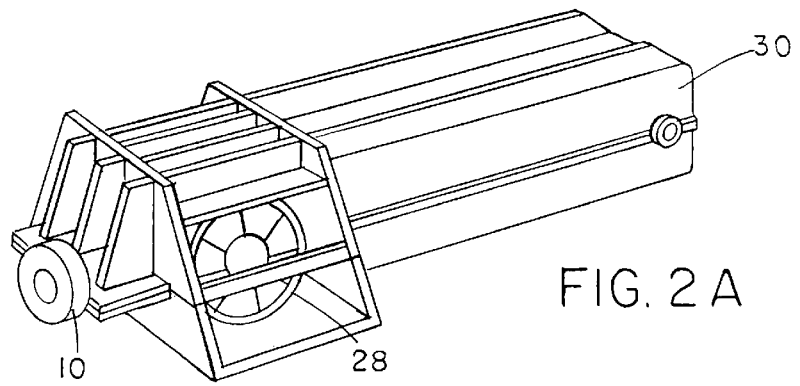
FIG. 2a is a perspective view of the exterior of the allergen detector housing.
Figure 2B:
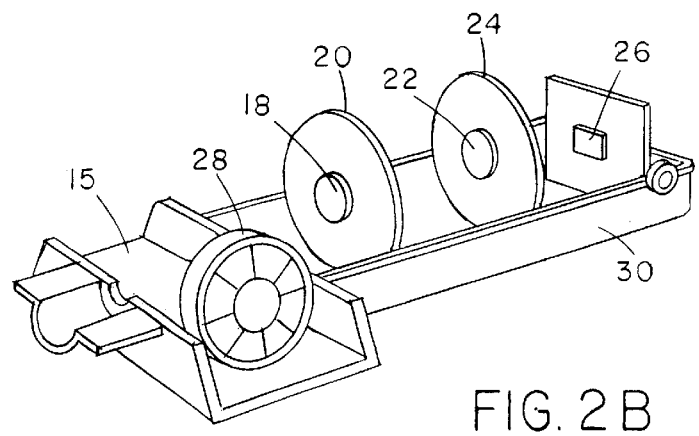
FIG. 2b is a view of the allergen detector with the top portion of the housing removed, revealing the internal elements thereof.

As shown in FIGS. 2a and 2b, fan 28 is used to periodically refresh air sample 15 within housing 30. In the preferred embodiment, air sample 15 is refreshed approximately every 30 seconds.

The output voltage of detector 26, in the preferred embodiment, is converted into a series of pulses over time, which are in turn counted by a logic circuit. An alarm is generated when a certain number of pulses are counted within a certain period of time. This alarm can be used, as in one embodiment of this invention, to provide an indication of poor air quality to a user of the device. In the preferred embodiment of this invention, the alarm is used to turn on an air filter having a blower and a HEPA filtration element. The unit is provided with a sensitivity level setting which can be used to vary the particle concentration within air sample 15 which must be detected before the alarm is generated and the unit turned on. In addition, an ionizer may be provided to negatively charge any particles which may not have been filtered by the filter element, and a manual override to allow the operation of the air filter independently of the allergen detection apparatus.

Housing 30, as shown in FIGS. 2a and 2b, consists of a generally tube-shaped casing in which the elements are mounted. An area is provided wherein an air sample 15 is drawn by fan 28. Preferably, the interior surface of housing 30 is finished to minimize the amount of light reflected therefrom, for, example, as a black matte finish, such that light scattered at or above the maximum scattering angle is absorbed by the walls of housing 30 and not reflected back into lens 20.

The majority of allergen particles to which individuals may be sensitive are in the size range of 5 to 50 microns, although a small quantity of allergen particles may be found at sized from 0.5 to 5 microns and from 50 to 500 microns. Thus, substantially all allergen particles will be found in the size range of 0.5 to 500 microns, with the maximum number being in the range of 5 to 50 microns. Therefore, the apparatus is preferably designed to detect particles in the size range of 0.5 to 500 microns.

The angle at which light is scattered by a particle 14 will be dependent on the wavelength of the light and the size of the particle. Airborne particles of different sizes have quite different light scattering properties. Larger particles will scatter light at smaller angles. For a red to infrared light source in the wavelength range of 0.6 micron to 1.0 micron, the smallest scattering angle for a particle size range of 0.5 to 50 microns is about 4° to 5° (see Electromagnetc Scattering, R. L. Rowell and R. S. Stein, ed., p. 140, Gordon and Breach 1965). If blocking member 18 is at a distance of L from the air sample, the radius of the central blocking portion should be L * tan (5°), in order to block light scattered at angles less than 5°, i.e. light scattered by particles larger than 50 microns. The blocking device can therefore be arranged to block all light scattered by particles of size greater than 50 microns.

Airborne particles are typically present in the air in a large range of sizes. As noted above, allergen particles such as pollen, dust, mold spores and the like are predominantly in the size range from 5 to 50 microns. Larger particles typically cannot pass through the nose and do not normally cause any problem. The system as illustrated in FIG. 1 is designed to discriminate between light scattered by particles in the allergen size range and light scattered by larger particles outside that range. Only particles with sizes comparable to the wavelength of the incident light will have well pronounced scattering maxima in the forward direction of light propagation.

This apparatus enables up to 99% of airborne allergen particles to be detected, while larger, non-allergeniic particles are not detected due to the design of the optical system for eliminating light scattered by particles of sizes outside the allergen size range of 0.5 to 50 microns. The user may readily adjust the allergen detection level. The apparatus is easy and inexpensive to manufacture, and simple to operate. It provides real time, accurate detection of excessive levels of allergen particles in the air, providing a warning to sensitive individuals who may need medication and also allowing allergen filtering equipment to be activated under such conditions to clean the air.

Although preferred embodiments of the present invention have been described above by way of example only, it will be understood by those skilled in the field that modifications may be made to the disclosed embodiments without departing from the scope of the invention, which is defined by the appended claims.

It is claimed:

1. A device for detecting allergen particles in environmental air comprising:

a light source having an optical axis wherein said light source directs a focused beam of light through a sample of said environmental air, whereby portions of said beam of light are scattered at various angles by particles of various sizes present in said sample of environmental air and whereby a portion of said beam of light remains unscattered;

a first circular member centered on said optical axis, said first circular member being of a diameter greater than or equal to the diameter of said focused beam of light, said first circular member being opaque to light of the wavelength emitted by said light source;

a second circular member centered on said optical axis, said second circular member being opaque to light of the wavelength emitted by said light source;

a first lens which focuses noise generated by said light source onto said second circular member and which transmits said scattered light such that said scattered light is not blocked by said second circular member;

a detector for measuring the quantity of light scattered by said particles in said sample of environmental air;

a second lens which focuses said scattered light onto said detector;

said first circular member adhering to the center of said first lens and said second circular member adhering to the center of said second lens; and said first and second circular members being of a darkened material having a fuzzy, non-flat surface texture.

2. The device of claim 1 wherein said darkened material is felt.

3. The device of claim 1 wherein said darkened material is comprises the loop half of a hook and loop fastener.

4. A device for detecting allergen particles in environmental air, comprising:

a light source having an optical axis wherein said light source directs a focused beam of light through a sample of said environmental air, whereby portions of said beam of light are scattered at various angles by particles of various sizes present in said sample of environmental air and whereby a portion of said beam of light remains unscattered;

a first circular member centered on said optical axis, said first circular member being of a diameter greater than or equal to the diameter of said focused beam of light, said first circular member being opaque to light of the wavelength emitted by said light source;

a second circular member centered on said optical axis, said second circular member being opaque to light of the wavelength emitted by said light source;

a first lens which focuses noise generated by said light source onto said second circular member and which transmits said scattered light such that said scattered light is not blocked by said second circular member;

a detector for measuring the quantity of light scattered by said particles in said sample of environmental air;

a second lens which focuses said scattered light onto said detector;

said focused beam of light having a cross-sectional area and said first and second circular members being shaped to correspond to said cross-sectional area of said focused beam of light.

* * * * *